(12) United States Patent
Ferenz et al.

(10) Patent No.: US 7,964,694 B2
(45) Date of Patent: Jun. 21, 2011

(54) POLYSILOXANES HAVING QUATERNARY AMMONIUM GROUPS, A PROCESS FOR THE PREPARATION THEREOF AND THE USE THEREOF IN CLEANING AND CARE FORMULATIONS

(75) Inventors: Michael Ferenz, Essen (DE); Sascha Herrwerth, Essen (DE); Holger Leidreiter, Hattingen (DE); Felix Mueller, Velbert (DE); Joerg Peggau, Essen (DE)

(73) Assignee: Evonik Goldschmidt GmbH (DE)

( * ) Notice: Subject to any disclaimer, the term of this patent is extended or adjusted under 35 U.S.C. 154(b) by 755 days.

(21) Appl. No.: 11/829,601

(22) Filed: Jul. 27, 2007

(65) Prior Publication Data
US 2008/0305065 A1 Dec. 11, 2008

(30) Foreign Application Priority Data
Jul. 31, 2006 (DE) .................... 10 2006 035 512

(51) Int. Cl.
*C08G 77/26* (2006.01)
(52) U.S. Cl. ................... 528/38; 424/59; 424/122
(58) Field of Classification Search ............. 528/38
See application file for complete search history.

(56) References Cited

U.S. PATENT DOCUMENTS

| 2006/0188455 A1* | 8/2006 | Ferenz et al. | 424/59 |
| 2008/0027202 A1* | 1/2008 | Ferenz et al. | 528/32 |
| 2010/0034765 A1* | 2/2010 | Herrwerth et al. | 424/70.122 |

FOREIGN PATENT DOCUMENTS

| DE | 1 493 384 | 1/1969 |
| DE | 33 40 708 | 5/1984 |
| DE | 37 19 086 | 10/1988 |
| DE | 101 07 772 | 9/2002 |
| DE | 103 270 871 | 1/2005 |
| EP | 0 282 720 | 9/1988 |
| EP | 0 294 643 | 12/1988 |
| EP | 1 439 200 | 7/2004 |

OTHER PUBLICATIONS

Mueller, Felix, Joerg Peggau, and Shoaib Arif. "Special Purpose Cleaning Formulations; Auto Care and Industrial/Institutional Products," *Handbook of Detergents: Part D: Formulation*. New York, CRC Press: 2005, pp. 261-268.

* cited by examiner

*Primary Examiner* — Randy Gulakowski
*Assistant Examiner* — Lindsay Nelson
(74) *Attorney, Agent, or Firm* — Frommer Lawrence & Haug LLP

(57) ABSTRACT

The invention relates to polysiloxanes of the general formula (I)

$$[M'D_n]_3 T \qquad (I),$$

in which:

M' is $XSiY_2O_{1/2}$
D is $SiY_2O_{2/2}$
T is $SiZO_{3/2}$ and a process for the preparation thereof and their use as additives in aqueous surfactant-containing formulations.

9 Claims, No Drawings

POLYSILOXANES HAVING QUATERNARY AMMONIUM GROUPS, A PROCESS FOR THE PREPARATION THEREOF AND THE USE THEREOF IN CLEANING AND CARE FORMULATIONS

The invention relates to novel polysiloxanes having quaternary ammonium groups and to a process for the preparation thereof. It furthermore relates to the use of these polymers as an additive in formulations for the care and cleansing of skin and integumentary appendages, such as, for example, as conditioners for hair, and for the cleaning and care of hard surfaces, such as an additive in vehicle washing.

Polysiloxanes having quaternary groups and the use thereof as an additive for hair care or textile softeners are known from the patent literature. Thus, for example, DE B 14 93 384 describes structures in which siloxanes are modified in the side groups with ammonium groups distributed randomly over the polymer. These compounds have the disadvantage that a pronounced silicone character is reduced and good activity is no longer observable.

Cationic silicones, as described in DE 37 19 086 and EP 0 282 720, have a more pronounced silicone character. EP 0 282 720 describes structures in which the quaternary functions are bonded terminally to the siloxane. Such compounds have advantages with regard to their action as a conditioner both for hair and textiles and for hard surfaces. Here, however, only two cationic centers are available, which often leads only to insufficient substantivity on the surface.

DE-A 33 40 708 discloses polyquaternary polysiloxane polymers. Polyquaternary polysiloxane polymers of this type do not have the disadvantages described above. However, the complicated preparation process for these compounds prevents them from being used in practice. The compounds can be prepared in yields of <60% of theory, which are economically unacceptable.

Human hair is exposed daily to a very wide range of influences. In addition to mechanical stresses due to brushing, combing, pinning up or tying back, the hairs are also attacked by environmental influences, such as, for example, strong UV radiation, cold, wind and water. The physiological status (e.g. age, health) of the respective person also influences the condition of the keratinic fibers.

In particular, the treatment with chemical compositions changes structure and surface properties of the hairs. Methods such as, for example, permanent waving, bleaching, coloring, tinting, smoothing, etc., but also frequent washing with aggressive surfactants are contributory factors in causing more or less damage to the hair structure. Thus, for example in the case of a permanent wave, both the cortex and the cuticula of the hair are attacked. The disulfide bridges of the cystine are broken by the reduction step and partly oxidized to cysteic acid in the subsequent oxidation step.

In bleaching, not only is the melanin destroyed but in addition from about 15 to 25% of the disulfide bonds of the cystine are oxidized in the case of a mild bleach. In the case of excessive bleaching, this may even be up to 45% (K. F. de Polo, A Short Textbook of Cosmetology, 2000, Verlag für chemische Industrie, H. Ziolkowsky GmbH). Thus, the chemical treatments, frequent washing or UV irradiation give rise to disadvantageous mechanical properties for the hair, caused by removal of naturally secreted hair fats or hair humectants (sebum). It therefore becomes brittle, dry, dull, porous and poorly combable.

In addition, thoroughly cleaned hair is usually very difficult to comb, both in the wet state and in the dry state, since the individual hairs tend to become frizzy and to knot. It therefore loses its resistance first during washing and subsequently during combing. This is evident from a significant decrease in the tensile strength in the case of wet hair. Moreover, it is less resistant than healthy hair to further damage by chemicals, surfactants and environmental influences.

For the care of such damaged hair, there are special preparations, such as, for example, conditioners, hair repair treatments, shampoos, leave-in conditioners, etc., which, however, can improve in particular the combability, the handle and the gloss of damaged hair. Such commercially available hair care compositions contain mainly alkylammonium-based cationic surfactants, polymers, waxes or oils or silicone oils. The activity of these compounds is due inter alia to the imparting of water repellency to the hair surface.

In the case of all these compositions, a good care effect (conditioning) of the hair is achieved but the appearance, in particular the gloss of the hair, is not improved by the care products and in some cases is even adversely affected.

There is therefore still a need for versatile active substances for personal hygiene and care compositions, such as shampoos, hair treatment compositions and hair aftertreatment compositions, which, in addition to the cleansing effect, improve the care of the hair and at the same time impart good gloss, which protect the hair from damage to the hair structure and which minimize the already caused structural damage to the hair, caused by environmental influences and shaping and coloring treatments.

It is an object of the invention to provide an active substance which is capable both of improving properties such as combability, softness, volume, shapeability, handling properties and untangling properties of undamaged and damaged hair and of imparting an attractive gloss to the hair. The compounds should therefore exhibit an improved or at least equally good individual effect, but overall an improved combined effect of mechanical and other properties.

The cleaning and care of hard surfaces in the private and commercial sector requires in some cases complex formulations and predetermined regulated work sequences. Thus, for example, the washing of vehicles in carwash installations consists as a rule of a plurality of successive processes which have to be exactly tailored to one another. This tailoring comprises, inter alia, the correct choice of the chemical formulations, compliance with the contact times, the mechanics of cleaning and the choice of temperature. Further literature: F. Müller, J. Peggau, S. Arif, Special Purpose Cleaning Formulations: Auto Care, in Handbook of Detergents, Part D: Formulation, M. Showell, ed. CRC Press, Boca Raton 2006, pages 261 to 278.

The actual cleaning, which can be divided into preliminary and main wash, it being possible to use different base formulations in each case, comprises the removal of the solid, insoluble dirt particles on the vehicle surface. For this purpose, there is a large number of formulations for a very wide range of cleaning methods. These formulations usually consist of anionic surfactant systems which, together with the basic or acidic components, introduce the tensioactivity required for the cleaning.

This cleaning is followed by the wash process in which cleaning agent residues have to be removed. This step serves as preparation for the use of a suitable drying agent which renders the vehicle water repellent before the final blow drying and thus enables the remaining water film to be more easily removed. The washing is important because drying agents have a cationic character and otherwise, after the use of anionic cleaning formulations, would form sparingly soluble salts which lead to unattractive spots on the vehicle and thus lead neither to desired gloss effect nor to water repellency.

Cationic surfactants form the substantial ingredients of these formulations where substantivity is required, i.e. persistence of the surface-active compound on the treated material. As in the case of applications in the area of fabric softeners, textile finishing or hair conditioners, this class of substances is also widely used in drier applications in carwash installations.

Since automotive coatings, like most surfaces, also have a negative electrical potential, the cationic surfactant is spread over the vehicle after the drying agent formulation has been sprayed on and displaces the water film present.

This process, which is referred to as "breaking", results in an association of the water film to form drops. These drops then run off the vehicle downward, both under their own gravitational force and as a result of the use of a blower in the last step of the car cleaning.

The formulation of drying aids for automatic vehicle cleaning presents the formulator with particular tasks.

Thus, the formulation not only must produce a spontaneous water break but should also lead to rapid drying a long-lasting gloss. What is important here is the correct concentration for use, which should be from about 0.1 to 0.3%. If the concentration is too low, the water film will not break; if it is too high, a smeary, greasy layer which can no longer lead to the desired gloss effect forms on the vehicle surface.

Even at low temperatures, the formulation should remain clear and without precipitates. In addition, the product must have a high water hardness tolerance in order to avoid leading to opaqueness both in hard and soft water and in recycled water. Any waxes, oils or other, water-immiscible care compositions used which are intended to remain on the surface must be emulsified.

A base formulation for a drier consists as a rule of quaternary ammonium compounds, so-called quats. Virtually exclusively environmentally friendly ester quats or imidazoline quats, in which the fat chain consists mainly of oleic acid, are used today. Since quats are generally not water-soluble, these highly unsaturated fat chains facilitate the formulation in aqueous systems.

In addition to quats, raw materials having emulsifying properties are also necessary for ensuring the abovementioned requirement profile.

In the course of accelerating the operation of carwash installations, various attempts have been made to accelerate the relatively tedious breaking process. For example, silicone compounds as described in DE 101 07 772 have been tested, but without success. Since one of the speed-determining steps in the carwash installation is the drying sequence, an acceleration will increase the throughput of vehicles in the washing installation and thus reduce waiting times for customers and increase the efficiency of the installation.

It is the object of this invention to find quaternary polysiloxane polymers which can be prepared in good yields and moreover, in the respective applications, have the desired property profile and exhibit a very good conditioning effect and gloss on hair.

It is furthermore the object of the invention to find quaternary polysiloxane polymers which can be prepared in good yield and moreover, in the respective applications, have the desired property profile and possess substantially accelerated breaking with simultaneous gloss retention in automotive care.

Surprisingly, it was found that polysiloxanes of the general formula I $[M'D_n]_3T$ do this.

The invention therefore relates to polysiloxanes of the general formula I $$[M'D_n]_3T \qquad \text{Formula I}$$

Here:

M' is $XSiY_2O_{1/2}$

D is $SiY_2O_{2/2}$

T is $SiZO_{3/2}$

X are identical or different organic radicals which carry ammonium functions,

Y are identical or different radicals from the group consisting of alkyl, aryl or alkaryl having 1 to 30 carbon atoms, preferably methyl or phenyl, in particular methyl, Z are identical or different radicals from the group consisting of alkyl, aryl or alkaryl having 1 to 30 carbon atoms, preferably methyl or phenyl, n is from 2 to 200, preferably from 3 to 120, in particular from 8 to 80.

Suitable radicals X are, for example, groups having the structure -R1-R2, in which R1 are preferably identical or different divalent radicals selected from the group consisting of

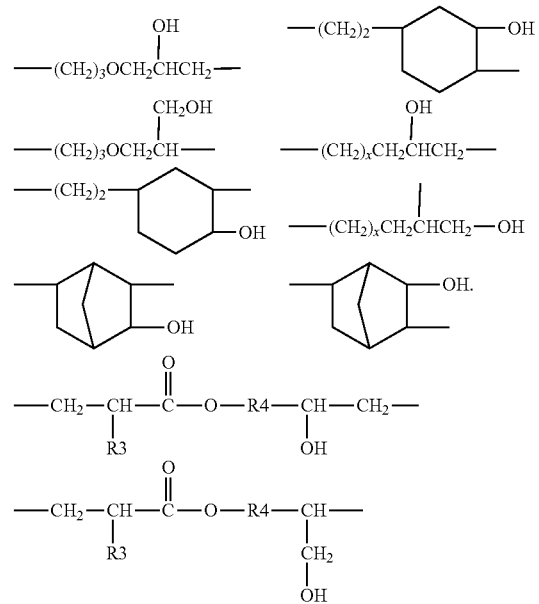

R1 is preferably:

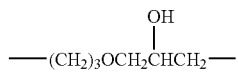

R2 is selected from the group consisting of

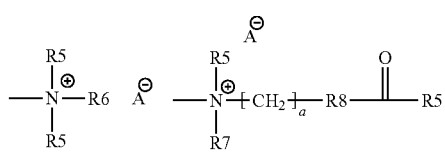

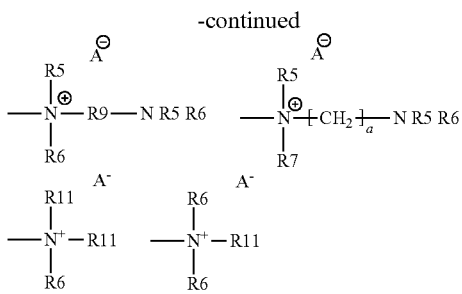

R3 are identical or different radicals from the group consisting of hydrogen or alkyl having 1 to 6 carbon atoms, preferably methyl, R4 are identical or different divalent hydrocarbon radicals which optionally contain ether functions, preferably methylene, R5, R6, R7 are, in each case, independently of one another, hydrogen or alkyl radicals having 1 to 30 carbon atoms, R8 are identical or different radicals from the group consisting of —O—; —NR10, R9 are identical or different optionally branched divalent hydrocarbon radicals, R10 are identical or different radicals from the group consisting of hydrogen or alkyl having 1 to 6 carbon atoms, R11 are identical or different radicals of the general formula:

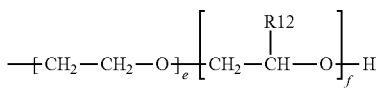

R12 are identical or different alkyl, aryl or alkaryl radicals having 1 to 30 carbon atoms which optionally contain ether functions, preferably methyl, ethyl or phenyl, in particular methyl, e is from 0 to 20, preferably from 0 to 10, in particular from 1 to 3, f is from 0 to 20, preferably from 0 to 10, e+f>=1, x is from 2 to 18, a is from 2 to 18, preferably 3, $A^-$ are identical or different counter ions to the positive charges on the quaternized nitrogen groups, selected from inorganic or organic anions of the acids HA, and of derivatives thereof.

It is familiar to the person skilled in the art that the compounds are present in the form of a mixture having a distribution substantially regulated by statistical laws.

The unit T is present on statistical average once in a polymer chain. However, a mixture of molecules is present so that a certain proportion of the molecules have no T units or a plurality of T units.

In a further preferred embodiment of the present invention, the counter ion $A^-$ to the positive charges on the quaternized nitrogen groups consists of the anion of a physiologically tolerated acid HA, which is particularly preferably selected from acetic acid, L-hydroxycarboxylic acid, in particular lactic acid, or aromatic carboxylic acids.

Further preferred counter ions originate from customary quaternizing agents. These are in particular ethyl sulfate, methyl sulfate, toluene sulfonate, chloride and bromide.

This invention furthermore relates to a process for the preparation of the products according to the invention. It proceeds from the equilibration of aryltris(dimethylsilyloxy)silane and/or alkyltris(dimethylsilyloxy)silane, in particular phenyltris(dimethylsilyloxy)silane and methyltris(dimethylsilyloxy)silane, with octamethylcyclotetrasiloxane and/or decamethylcyclopentasiloxane (cyclic compounds). Suitable methods for equilibrating siloxanes are described, for example, in the patent EP 1 439 200.

The content of the abovementioned patent literature on equilibration is hereby introduced as a reference and is considered to be part of the disclosure content of the present application.

In addition to the cyclic siloxanes, α,ω-di-SiH-functional siloxanes and nonfunctional siloxanes can also be added during equilibration to the equilibration mixture in order to reduce the average degree of modification in a controlled manner.

Epoxides containing double bonds, such as, for example allyl glycidyl ether, can subsequently be hydrosilylated with the SiH-functional siloxanes thus obtained. The use of Pt, Rh or Ru catalysts for the hydrosilylation is known to the person skilled in the art.

The epoxy silanes thus obtained can finally be reacted with tertiary amines to give the desired siloxanes carrying quaternary ammonium functions.

It is known to the person skilled in the art that secondary reactions are to be expected in such a reaction sequence, both in the equilibration of the SiH functional siloxanes and in the hydrosilylation and quaternization. The extent of the secondary reactions depends inter alia on the type of starting materials as well as on the reaction conditions. Thus, for example, the degree of quaternization in the reaction of epoxy siloxanes with tertiary amines in the presence of carboxylic acids by customary methods is from about 80 to 95%.

This invention furthermore relates to the use of the compounds of the general formula I and of the compounds of general formula I which are prepared by the process according to the invention or of the industrial mixtures prepared by this process as an additive in optionally surfactant-containing aqueous care and cleaning formulations.

This invention furthermore relates to the use of the compounds of the general formula I and of the compounds of the general formula I which are prepared by the process according to the invention or of the industrial mixtures prepared by this process as conditioners for hair treatment compositions and hair aftertreatment compositions and as compositions for improving the hair structure.

This invention furthermore relates to the use of the compounds of the general formula I and of the compounds of the general formula I which are prepared by the process according to the invention or of the industrial mixtures prepared by this process for the preparation of gloss-improving care formulations.

This invention furthermore relates to hair treatment compositions and hair aftertreatment compositions for washing out or for remaining in the hair, for example shampoos with or without a pronounced conditioning effect, 2-in-1 shampoos, conditioners, hair repair treatments, hair masks, hair styling aids, styling compositions, blow drying lotions, hair setting compositions, permanent wave compositions, hair smoothing compositions and compositions for coloring the hair. Depending on the intended use, these are compositions containing from 2 to 25% by weight of one or more detergent surfactants from the group consisting of the anionic, nonionic, amphoteric or zwitterionic surfactants, from 0.5 to 10% by weight of one or more emulsifiers, from 0.5 to 10% by weight of one or more consistency regulators, from 0.5 to 10% by weight of one or more preferably cationic surfactants or emulsifiers, from 1 to 20% by weight of one or more cosmetic oils, silicone oils or emollients and customary auxiliaries and additives in customary concentrations, and additionally containing one or more active substances for hair cosmetics, selected from the group consisting of cationic polymers, such as, quaternized cellulose and derivatives thereof, chitosans and derivatives thereof, cationic alkyl glycosides, cationic guar derivatives, polymers of dimethyldiallylammonium salts and copolymers thereof with esters and amides of acrylic acid and methacrylic acid, copolymers of vinylpyrrolidone with quaternized derivatives of dialkylaminoalkyl acrylate and methacrylate, such as, for example, diethyl sulfate-quaternized vinylpyrrolidone/dimethylaminoethyl methacrylate copolymers, vinylpyrrolidone/vinylimidazolium methochloride copolymers, terpolymers of the monomers of vinylpyrrolidone, caprolactam and acrylamides, quaternized polyvinyl alcohol and those polymers which are known by the INCI-designation polyquaternium-2, polyquaternium-17, polyquaternium-18, polyquaternium-27 and polyquaternium-37, cationic or nonionic protein hydrolysis products of vegetable or animal origin, based on keratin, collagen, elastin, wheat, rice, soybean, milk, silk or corn, or further silicone derivatives, such as, for example, dimethiconol or dimethicone (INCI designation for polydimethylsiloxanes) and modified silicones which may be terminally functionalized (INCI prefix bis-) and/or graft-functionalized, such as, for example, alkoxysilicones and alkylsilicones having long-chain alkyl groups, polyoxyalkyl-modified silicones, such as PEG/PPG-3/10 dimethicone or bis-PEG/PPG-20/20 dimethicone with or without alkyl ether group and esters thereof, such as, for example, dimethicone PEG-7 cocoate, and polyfunctionalized silicones, such as, for example, cetyl PEG/PPG-10/1 dimethicone or methyleugenyl PEG-8 dimethicone, and moreover silicone copolymers with acrylates, including those copolymers with and without alkyl modification, branched silicone derivatives, such as dimethicone/silsesquioxane copolymer, crosslinked silicone copolymers, such as dimethicone crosspolymer, alkyl dimethicone/divinyl dimethicone crosspolymer, cetearyl dimethicone crosspolymer or cetearyl dimethicone/vinyl dimethicone crosspolymer, amino-functionalized silicones, such as amodimethicone, aminopropyl dimethicone, PEG-7 amodimethicone, methoxy PEG/PPG-7/3 aminopropyl dimethicone, or ionically modified silicones, such as dimethicone propyl PG-betaine, vitamins, panthenol, pyrrolidonecarboxylic acid, bisabolol, plant extracts, creatine, ceramides and UV-absorbing compositions, which contain an effective amount of at least one compound of the general formula (I).

This invention furthermore relates to the use of the compounds of the general formula I and of the compounds of the general formula I which are prepared by the process according to the invention or of the industrial mixtures prepared by this process for the preparation of formulations for the cleaning and care of hard surfaces, preferably for the cleaning and care of vehicles, in particular as an additive in drying aids for car washing installations.

WORKING EXAMPLES

The following examples are intended for clarifying the invention but they by no means constitute a limitation.

Example 1 a) Equilibration of an SiH-Functional Polysiloxane
In a 500 ml three-necked flask, 8.2 g of phenyltris(dimethylsiloxy)silane, 334 g of decamethylpentasiloxane and 0.34 g of an acidic catalyst were mixed and were stirred for 4 hours at 80° C. After cooling, 20 g of NaHCO$_3$ were added and stirring was effected at room temperature for 12 hours. After filtration, a clear product having an SiH value of 0.02% was obtained.

b) Preparation of an Epoxysiloxane
In a 500 ml three-necked flask, 300 g of the compound prepared under 1 a) and 7.5 g of allyl glycidyl ether were initially taken together and heated to 100° C. Thereafter, 15 ppm of a platinum catalyst were added and stirring was effected for two hours. After a subsequent reaction, a clear product having an epoxy value of 0.37% was obtained.

c) Conversion into the Quaternized Polysiloxane Polymer
In a 500 ml three-necked flask, 14.5 g of 3-N,N-dimethylaminopropyllauramide, 2.7 g of acetic acid and 120 g of isopropanol were stirred at room temperature. 200 g of the compound prepared according to 1 b) were then added dropwise. Thereafter, stirring was carried out for 8 hours at 50° C. and distillation was effected. A turbid highly viscous liquid was obtained, which is described by the following statistical formula:

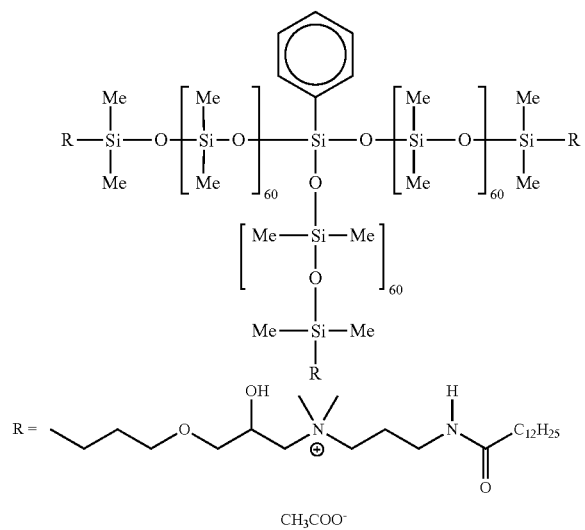

The person skilled in the art is familiar with the fact that the abovementioned formula represents an idealized structural formula. Linear and more highly branched structures are additionally present in the product.

Example 2 a) Equilibration of an SiH-Functional Polysiloxane
In a 1000 ml three-necked flask, 50 g of phenyltris(dimethylsiloxy)silane, 667 g of decamethylpentasiloxane and 0.7 g of an acidic catalyst were mixed and were stirred for 4 hours at 80° C. After cooling, 15 g of NaHCO$_3$ were added and stirring was effected at room temperature for 12 hours. After filtration, a clear product having an SiH value of 0.07% was obtained.

b) Preparation of an Epoxysiloxane
In a 1000 ml three-necked flask, 670 g of the compound prepared under 2 a) and 65 g of allyl glycidyl ether were initially taken together and heated to 100° C. Thereafter, 15 ppm of a platinum catalyst were added and stirring was effected for two hours. After a subsequent reaction, a clear product having an epoxy value of 0.99% was obtained.

c) Conversion into the Silicone Quat

In a 1000 ml three-necked flask, 63 g of N,N-dimethylstearylamine, 12 g of acetic acid and 200 g of isopropanol were stirred at room temperature. 325 g of the compound prepared according to 2 b) were then added dropwise. Thereafter, stirring was carried out for 8 hours at 60° C. and distillation was effected. A turbid highly viscous liquid was obtained, which is described by the following statistical formula:

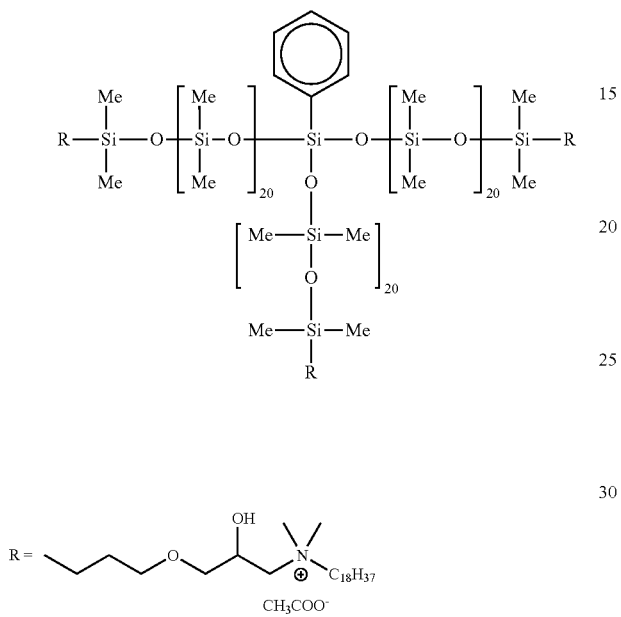

The person skilled in the art is familiar with the fact that the abovementioned formula represents an idealized structural formula. Linear and more highly branched structures are additionally present in the product.

Example 3 a) Equilibration of an SiH-Functional Polysiloxane

In a 500 ml three-necked flask, 33.1 g of phenyltris(dimethylsiloxy)silane, 274.4 g of decamethylpentasiloxane and 0.3 g of an acidic catalyst were mixed and were stirred for 4 hours at 80° C. After cooling, 10 g of NaHCO$_3$ were added and stirring was effected at room temperature for 12 hours. After filtration, a clear product having an SiH value of 0.097% was obtained.

b) Preparation of an Epoxysiloxane

In a 250 ml three-necked flask, 103.5 g of the compound prepared under 3 a) and 15 g of allyl glycidyl ether were initially taken together and heated to 100° C. Thereafter, 15 ppm of a platinum catalyst were added and stirring was effected for two hours. After a subsequent reaction, a clear product having an epoxy value of 1.4% was obtained.

c) Conversion into the Silicone Quat

In a 500 ml three-necked flask, 32 g of 3-N,N-dimethylaminopropyllauramide, 6.2 g of acetic acid and 100 g of isopropanol were stirred at room temperature. 115 g of the compound prepared according to 3 b) were then added dropwise. Thereafter, stirring was carried out for 8 hours at 60° C. and distillation was effected. A turbid highly viscous liquid was obtained, which is described by the following statistical formula:

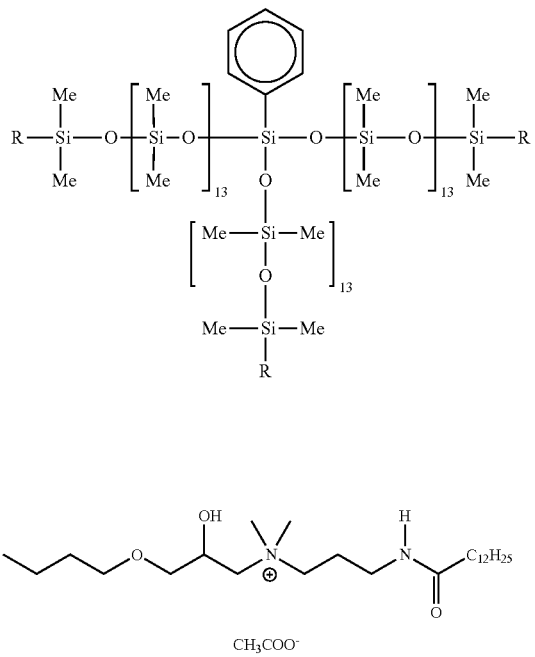

The person skilled in the art is familiar with the fact that the abovementioned formula represents an idealized structural formula. Linear and more highly branched structures are additionally present in the product.

Example 4 a) Equilibration of an SiH-Functional Polysiloxane

In a 500 ml three-necked flask, 3.3 g of phenyltris(dimethylsiloxy)silane, 220.4 g of decamethylpentasiloxane and 0.3 g of an acidic catalyst were mixed and were stirred for 4 hours at 80° C. After cooling, 4.5 g of NaHCO$_3$ were added and stirring was effected at room temperature for 12 hours. After filtration, a clear product having an SiH value of 0.013% was obtained.

b) Preparation of an Epoxysiloxane

In a 1000 ml three-necked flask, 752 g of the compound prepared under 4 a) and 14.8 g of allyl glycidyl ether were initially taken together and heated to 100° C. Thereafter, 15 ppm of a platinum catalyst were added and stirring was effected for two hours. After a subsequent reaction, a clear product having an epoxy value of 0.21% was obtained.

c) Conversion into the Silicone Quat

In a 250 ml three-necked flask, 3.2 g of 3-N,N-dimethylaminopropyllauramide, 0.62 g of acetic acid and 50 g of isopropanol were stirred at room temperature. 76.2 g of the compound prepared according to 4 b) were then added dropwise. Thereafter, stirring was carried out for 8 hours at 60° C. and distillation was effected. A turbid highly viscous liquid was obtained, which is described by the following statistical formula:

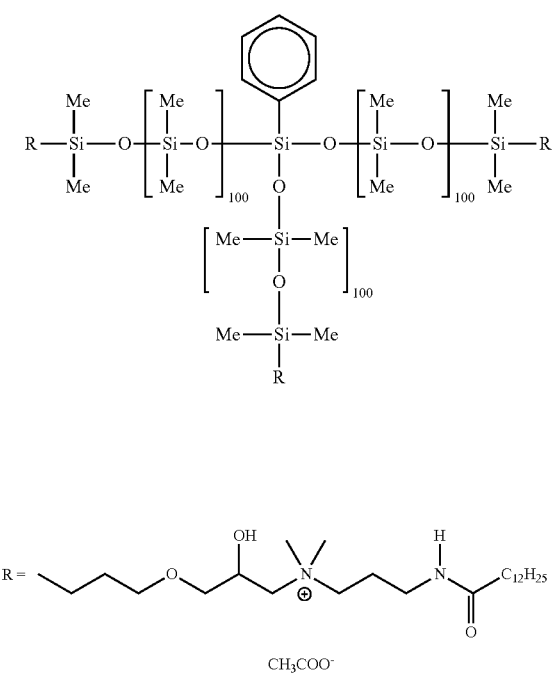

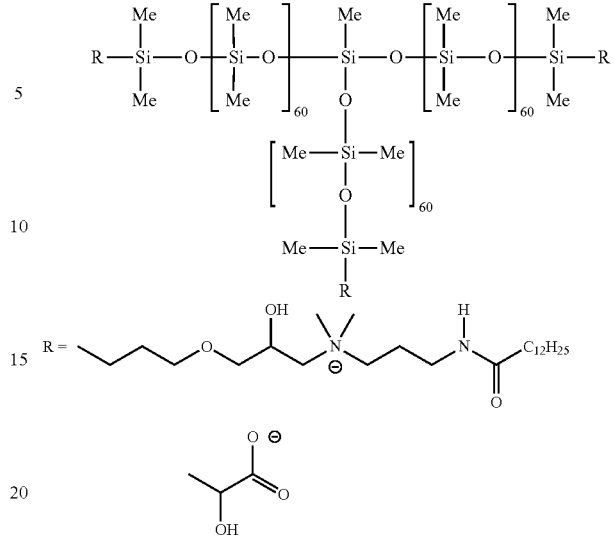

The person skilled in the art is familiar with the fact that the abovementioned formula represents an idealized structural formula. Linear and more highly branched structures are additionally present in the product.

Example 5 a) Equilibration of an SiH-Functional Polysiloxane

In a 500 ml three-necked flask, 6.7 g of methyltris(dimethylsiloxy)silane, 334 g of decamethylpentasiloxane and 0.4 g of an acidic catalyst were mixed and were stirred for 5 hours at 80° C. After cooling, 20 g of NaHCO$_3$ were added and stirring was effected at room temperature for 12 hours. After filtration, a clear product having an SiH value of 0.02% was obtained.

b) Preparation of an Epoxysiloxane

In a 1000 ml three-necked flask, 450 g of the compound prepared under 5 a) and 11.3 g of allyl glycidyl ether were initially taken together and heated to 100° C. Thereafter, 15 ppm of a platinum catalyst were added and stirring was effected for two hours. After a subsequent reaction, a clear product having an epoxy value of 0.37% was obtained.

c) Conversion into the Quaternary Polysiloxane Polymer

In a 1000 ml three-necked flask, 31.9 g of 3-N,N-dimethylaminopropyllauramide, 8.9 g of lactic acid and 200 g of isopropanol were stirred at room temperature. 440 g of the compound prepared according to 5 b) were then added dropwise. Thereafter, stirring was carried out for 8 hours at 50° C. and distillation was effected. A turbid highly viscous liquid was obtained, which is described by the following statistical formula:

The person skilled in the art is familiar with the fact that the abovementioned formula represents an idealized structural formula. Linear and more highly branched structures are additionally present in the product.

Performance Characteristics

Use in Cosmetics

Preparation and testing of hair treatment compositions using compounds 1, 2, 3, 4 and 5 according to the invention.

For assessing the component characteristics, hair braids which are used for the sensory tests are damaged beforehand in a standardized manner by a permanent wave treatment and a bleach treatment. For this purpose, products customary for hair dressing are used. The test sequence, the base materials used and the details of the assessment criteria are described in DE 103 27 871.

Test Formulations

For assessing the performance characteristics, the compounds according to the invention and comparative products are used in simple cosmetic formulations.

The performance characteristics during use in a shampoo were tested in the following formulation:

| Product | Amounts by weight |
|---|---|
| Sodium lauryl ether sulfate (28% strength) e.g. TEXAPON NSO (Cognis) | 32% |
| "Conditioner" | 0.5% |
| TEGO betaine F Cocamidopropyl betaine (30%) | 10% |
| Cationic polymer for improving the efficiency of conditioners (cationic deposition polymer) (e.g. guar hydroxypropyl trimonium chloride, polyquaternium-10) | 0.3% |
| Water | to 100% |
| Citric acid | to pH 6.0 ± 0.3 |

For evaluating the properties of the shampoo formulation, no aftertreatment with a conditioner was carried out in the test sequence.

In addition the products according to the invention were also tested in a simple hair conditioner having the following composition:

| Product | Amounts by weight |
|---|---|
| TEGINACID ® C | 0.5% |
| Ceteareth-25 | |
| TEGO ® Alkanol 16 | 2.0% |
| Cetyl alcohol | |
| "Conditioner" | 1.0% |
| VARISOFT ® 300 | 3.3% |
| Cetrimonium chloride (30%) | |
| Water | to 100% |
| Citric acid | to pH 4.0 ± 0.3 |

In testing the properties of hair conditioners, the hair was pretreated by a shampoo which contains no conditioner.

The compound examples according to the invention, comparative products or combinations of compounds according to the invention and known conditioners (in particular cetrimonium chloride) are designated "conditioners".

Standardized treatment of predamaged hair strands using conditioning samples:
the hair strands predamaged as described above are treated as follows with the shampoo described above or the conditioner described above:
the hair strands are wetted under running, warm water. The excess water is pressed out gently by hand, then the shampoo is applied and rubbed gently into the hair (1 ml/hair strand (2 g)). After a residence time of 1 min, the hair is washed for 1 min. If appropriate, a conditioner is applied directly thereafter and worked gently into the hair (1 ml/hair strand (2 g)). After a residence time of 1 min, the hair is washed for 1 min.

Before the sensory assessment, the hair is dried in the air at 50% relative humidity and 25° C. for at least 12 hours.

In order to avoid influencing the test results by (usually present) formulation constituents, the composition of the test formulations is deliberately chosen to be simple. Formulations according to the invention may contain further ingredients in addition to said ingredients and/or instead of said ingredients. In particular, the combination with further ingredients can lead to a synergistic improvement in the case of the effects described. Such ingredients may be (but are not limited thereto):
surfactants, wetting agents or emulsifiers from the groups consisting of the anionic, cationic, zwitterionic, amphoteric or nonionic surface-active substances, such as fatty alcohol sulfates, fatty alcohol ether sulfates, alkylsulfonates, alkylbenzenesulfonates, alkylsulfosuccinates, quaternary ammonium salts, alkylbetaines, fatty acid amidoalkyl betaines, derivatives of monomeric or condensed saccharides, such as sugar esters, methyl or ethylglucoside fatty acid esters, alkylglucosides, ethoxylated fatty alcohols, fatty acid alkanolamides or ethoxylated fatty acid esters, thickeners, such as kaolin, bentonite, fatty acids, fatty alcohols, starch, polyacrylic acid and their derivatives, cellulose derivatives, guar derivative, alginates, chitosan, vaseline or paraffin, and furthermore opacifiers, such as, for example glycol ester derivatives or alcohols, such as ethanol, propanol, isopropanol, propylene glycol or glycerol, solubilizers, stabilizers, buffer systems, perfume oils, dyes and in particular also further conditioners and care additives, such as other cationic or amphoteric polymers, lanolin and its derivatives, cholesterol, ceramides, pantothenic acid, betaines, creatine, other silicones or silicone derivatives.

Assessment Criteria

The sensory evaluations are effected according to ratings which are allocated on a scale of 1 to 5, 1 being the poorest and 5 being the best evaluation. The individual test criteria each receive a separate evaluation.

The test criteria are: wet combability, wet handle, dry combability, dry handle, appearance/gloss.

In the following table, the results of the sensory assessment of the treatment of the hair strands with substances according to the invention or placebo, carried out as described above, are compared.

In the shampoo application, guar hydroxypropyltrimonium chloride ("guar quat") was used as a cationic polymer

| Formulation of "simple shampoo" with | Wet combability | Wet handle | Dry combability | Dry handle | Gloss |
|---|---|---|---|---|---|
| Compound 1 according to the invention | 4.0 | 3.8 | 4.3 | 4.3 | 3.9 |
| Compound 2 according to the invention | 3.5 | 4.0 | 4.4 | 4.3 | 4.1 |
| Compound 3 according to the invention | 3.5 | 3.3 | 4.2 | 4.0 | 3.0 |
| Compound 4 according to the invention | 3.0 | 3.0 | 3.5 | 3.8 | 3.0 |
| Compound 5 according to the invention | 4.0 | 3.8 | 4.5 | 4.3 | 3.9 |
| Comparative compound quaternium-80 (ABIL ® Quat 3272, Goldschmidt GmbH) | 3.0 | 3.0 | 3.0 | 3.5 | 3.0 |
| Control without conditioner but with "guar quat" | 2.3 | 2.5 | 2.8 | 3.3 | 2.3 |
| Control shampoo without conditioner | 1.5 | 1.5 | 1.3 | 2.8 | 3.5 |

The results surprisingly show that the compounds according to the invention of examples 1 and 2 receive significantly better evaluations than the comparative product "quaternium-80". The compounds according to the invention of examples 3 and 4 show the same good activity as quaternium-80. The good evaluation of the gloss properties of all compounds according to the invention should be particularly singled out.

| Formulation of "simple conditioner" with | Wet combability | Wet handle | Dry combability | Dry handle | Gloss |
|---|---|---|---|---|---|
| Compound 1 according to the invention | 4.5 | 4.0 | 4.5 | 4.5 | 4.2 |
| Compound 2 according to the invention | 4.5 | 4.5 | 4.5 | 4.5 | 3.8 |
| Compound 3 according to the invention | 4.0 | 4.25 | 4.5 | 4.2 | 2.8 |
| Compound 4 according to the invention | 4.5 | 4.5 | 4.0 | 4.8 | 3.8 |

-continued

| Formulation of "simple conditioner" with | Wet combability | Wet handle | Dry combability | Dry handle | Gloss |
|---|---|---|---|---|---|
| Compound 5 according to the invention | 4.6 | 4.0 | 4.6 | 4.5 | 4.2 |
| Control without compound according to the invention | 4.3 | 3.5 | 4.0 | 3.8 | 2.4 |
| Control without compound according to the invention and without cetrimonium chloride | 1.3 | 1.7 | 2.0 | 2.8 | 2.8 |

In the conditioner application, too, the compounds according to the invention show very good cosmetic evaluations in the sensory assessment. Particularly in the evaluations for wet handle and dry handle, the already good performance of cetrimonium chloride is even further increased by the combination with the compounds according to the invention. A significantly better evaluation is also achieved in the gloss.

In general, it is also found that the skin sensation on the hands is substantially improved during and after the application if compounds according to the invention are present in the formulation. Particularly in O/W emulsions, the skin sensation can be improved by the compounds according to the invention.

Thus, in the example formulation, a substantially more pleasant skin sensation is achieved by the use of the compound according to the invention.

| Phase | | % by weight |
|---|---|---|
| A | Water | 74.57 |
|   | NaCl | 0.08 |
| B | Glycerol | 7.65 |
|   | Compound 5 according to the invention | 0.50 |
| C | Distearyldimonium chloride | 4.25 |
|   | Petrolatum | 4.55 |
|   | Isopropyl palmitate | 4.25 |
|   | Cetyl alcohol | 3.75 |
|   | Dimethicone | 0.40 |
| D | Preservative | q.s. |
|   | Citric acid | to pH 4.2 to 4.3 |

Preparation:
Mix phase A and heat to 70° C. Homogeneously mix phase B and stir into phase A, keep at 70° C. Add the ingredients of phase C in succession to the combination of phases A and B and in each case stir homogeneously during each addition. Keep the temperature at 70° C. during this procedure. Then homogenize the complete mixture for about 2 minutes. Cool with stirring and if appropriate add preservative.

The invention therefore furthermore relates to the use of the compounds according to the invention in formulations for the cleansing and care of the skin, such as, for example, shower products, bath products and liquid soaps.

Use in Automotive Care

This invention furthermore relates to the use of compounds according to the invention in commercial car washing in drying auxiliaries in the car washing installation. Here, the cleaning step carried out with anionic surfactants is followed by a treatment with a cationic composition which ensures gloss and water repellency on the automotive coating and at the same time permits the subsequent drying of the vehicle by a blower. In car washing installations, the contact time of this composition is of particular importance for increasing the throughput of vehicles and hence the efficiency. The use of compounds according to the invention was tested in formulations complying with practical requirements, a considerable shortening of the breaking time surprisingly being observed, also in comparison with quaternary silicone compounds known from the literature.

The following base formulation was tested:

| | |
|---|---|
| Butyldiglycol | 8.5% |
| Dipropylene glycol butyl ether | 5.5% |
| 9-Octadecenoic acid (Z)-, reaction products with triethanolamine, dimethyl sulfate-quaternized | 12.0% |
| Octyl palmitate | 5.0% |
| Acetic acid | 0.5% |
| Water to 100 | |

Formulation 8
The base formulation is formulation No. 8.
Formulation 9
The base formulation comprising 0.8% of active substance quaternary silicone compound according to patent EP 0 294 643 is formulation 9.
Formulation 10
The base formulation comprising 0.8% of active substance quaternary silicone compound according to this document with N=50 is formulation 10.
Formulation 11
The base formulation comprising 0.8% of active substance quaternary silicone compound according to this document with N=80 is formulation 11.

These formulations are diluted 1:1000 with tap water in conformity with practical requirements, and the breaking behavior of the dilutions was investigated.

Characteristic of the efficiency is the breaking of the water film on the automotive coating as well as the glass surfaces of the vehicle after the addition of the drying agent. Whereas a determination of the breaking on coated surfaces is difficult to reproduce, glass surfaces are very suitable for this purpose.

The breaking behavior was determined as follows:

The time which was required to penetrate a defined water film on glass and to dewet the glass is measured. The first reaction time and the complete penetration of the water on a slide are recorded.

Mirror tile
Slide 76×26 mm (3×1 inch)
Pipette 3 ml plastic
Metering pipette 100 μl
Water of defined quality; conductivity value
Stopwatch
Bunsen burner Samples are measured as stated in dilution in water, generally in a 1:1000 dilution. Dust is removed from the slide and the latter is treated briefly over a flame in order to ensure an absolutely clean residue-free surface.

0.5 ml of water is applied as a uniform film to the slide with the aid of a pipette. If a film cannot be formed, the slide must be cleaned again or discarded. Thereafter, 50 μl of the drying aid dilution used is applied centrally to the water surface and the stopwatch is started. The beginning of dewetting and the breakthrough of the retracting water on the 26 mm side are recorded. This makes it possible to record the reaction time and the breaking speed.

The data are stated in seconds.
The table shows the following results:

| | Beginning of breaking | End of breaking |
|---|---|---|
| Dilution from formulation 8 | 10 s | 30 s |
| Dilution from formulation 9 | 15 s | 30 s |
| Dilution from formulation 10 | 3 s | 15 s |
| Dilution from formulation 11 | 7 s | 25 s |

It is found that in particular the breaking with the compound according to the invention with N=50 has a considerable effect.

The following table can be used for scaling:

| Beginning of breaking | | End of breaking | |
|---|---|---|---|
| optimum | <10 s | good | <10 s |
| good | 11-20 s | optimum | 11-20 s |
| moderate | 21-45 s | good | 21-30 s |
| poor | >45 s | moderate | 31-45 s |
| | | poor | <45 s |

The breaking should not end too rapidly since otherwise poorly removable microdrops form and leave behind traces after drying.

At the same time, the compounds have a visibly positive effect on the gloss of the dried vehicle.

The invention claimed is:
1. A polysiloxane of the general formula I:

$$[M'D_n]_3 T \qquad \text{formula I}$$

in which the substituents and indices are:
$M' = XSiY_2O_{1/2}$
$D = SiY_2O_{2/2}$
$T = SiZO_{3/2}$
X=identical or different organic radicals carrying ammonium functions,
Y=identical or different radicals from the group consisting of alkyl, aryl or alkaryl having 1 to 30 carbon atoms,
Z=identical or different radicals from the group consisting of alkyl, aryl or alkaryl having 1 to 30 carbon atoms,
n=from 2 to 200
wherein,
wherein
X=-R1-R2, where
R1 are identical or different divalent radicals selected from the group consisting of

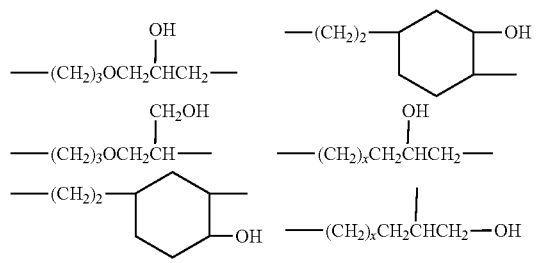

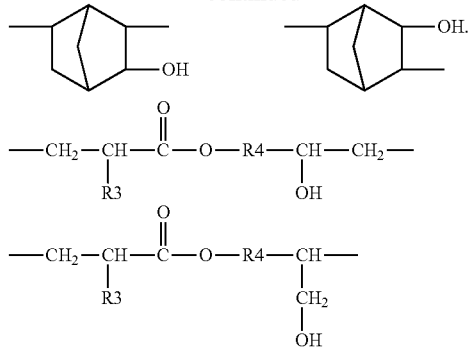

R2 is selected from the group consisting of

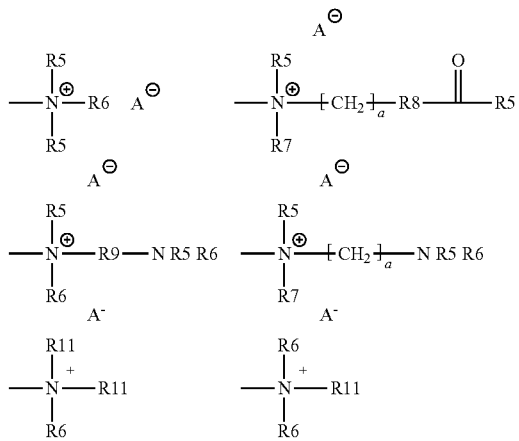

R3 are identical or different radicals from the group consisting of hydrogen or alkyl having 1 to 6 carbon atoms,
R4 are identical or different divalent hydrocarbon radicals which optionally contain ether functions,
R5, R6, R7 are, in each case independently of one another, hydrogen or alkyl radicals having 1 to 30 carbon atoms,
R8 are identical or different radicals from the group —O; —NR10,
R9 are identical or different optionally branched divalent hydrocarbon radicals,
R10 are identical or different radicals from the group consisting of hydrogen or alkyl having 1 to 6 carbon atoms,
R11 are identical or different radicals of the general formula:

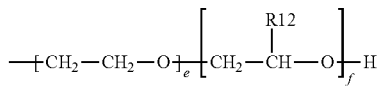

R12 are identical or different alkyl, aryl or alkaryl radicals having 1 to 30 carbon atoms which optionally contain ether functions,
e is from 0 to 20,
f is from 0 to 20, e+f>=1,
x is from 2 to 18,
a is from 2 to 18,
A⁻ are identical or different counter ions to the positive charges on the quaternized nitrogen groups, selected from inorganic or organic anions of the acids HA, and derivatives thereof.

2. The polysiloxane as claimed claim 1, wherein R1 has the meaning

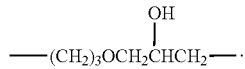

3. A process for the preparation of polysiloxanes as claimed in any of claims 1 to 2, wherein first aryltris(dimethylsilyloxy)silanes and/or alkyltris-(dimethylsilyloxy)silanes are equilibrated with cyclic siloxane compounds, epoxides containing double bonds are then hydrosilylated with the resulting SiH-functional equilibration product, and the epoxy siloxanes thus obtained are finally reacted with tertiary amines to give the corresponding quaternary siloxanes.

4. The polysiloxane of claim 2, wherein
Y=methyl or phenyl;
Z=methyl or phenyl;
n=3 to 120;
R12=methyl, ethyl or phenyl;
e=0 to 10; and
f=0 to 10.

5. The polysiloxane of claim 4, wherein
Y=methyl;
n=8 to 80;
R12=methyl;
e=1 to 3; and
a=3.

6. The polysiloxane of claim 5, wherein R2 is

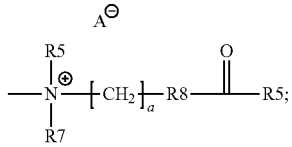

R5 is methyl or C12 alkyl;
R7 is methyl;
R8 is NR10; and
R10 is hydrogen.

7. The polysiloxane of claim 6, wherein
A$^-$ is selected from the group consisting of acetic acid, L-hydroxycarboxylic acid and aromatic carboxylic acid.

8. A method of providing conditioning effect and gloss on hair which comprises of administering an effective amount of the polysiloxane of claim 7.

9. A method of enhancing the breaking effect and gloss retention of a car care formulation which comprises of adding an effective amount of the polysiloxane of claim 7.

* * * * *